US009598516B2

(12) United States Patent
Castro et al.

(10) Patent No.: US 9,598,516 B2
(45) Date of Patent: Mar. 21, 2017

(54) CATALYST

(71) Applicant: BOREALIS AG, Vienna (AT)

(72) Inventors: Pascal Castro, Helsinki (FI); Ville Virkkunen, Helsinki (FI); Vyatcheslav Izmer, Moscow (RU); Dmitry Kononovich, Moscow (RU); Alexander Voskoboynikov, Moscow (RU); Luigi Resconi, Ferrara (IT)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 14/654,401

(22) PCT Filed: Dec. 19, 2013

(86) PCT No.: PCT/EP2013/077344
§ 371 (c)(1),
(2) Date: Jun. 19, 2015

(87) PCT Pub. No.: WO2014/096171
PCT Pub. Date: Jun. 26, 2014

(65) Prior Publication Data
US 2015/0344595 A1    Dec. 3, 2015

(30) Foreign Application Priority Data

Dec. 21, 2012    (EP) .................................... 12199251

(51) Int. Cl.
C08F 4/6592    (2006.01)
C08F 110/06    (2006.01)
C07C 1/32    (2006.01)
C07F 17/00    (2006.01)
C08F 10/06    (2006.01)
C07F 7/08    (2006.01)
C08F 4/659    (2006.01)

(52) U.S. Cl.
CPC ............ C08F 110/06 (2013.01); C07C 1/326 (2013.01); C07F 7/0818 (2013.01); C07F 17/00 (2013.01);
(Continued)

(58) Field of Classification Search
CPC  C08F 4/65927; C08F 210/06; C08F 4/65912; C08F 10/061
See application file for complete search history.

(56) References Cited

U.S. PATENT DOCUMENTS 6,787,618 B1    9/2004    Winter et al.
7,405,261 B2    7/2008    Schulte et al.
(Continued)

FOREIGN PATENT DOCUMENTS

EP    0537686 A1    4/1993
EP    0776913 A2    6/1997
(Continued)

OTHER PUBLICATIONS

Deng, H. et al., Synthesis of High-Melting, Isotactic Polypropene with C2-Symmetrical Zirconocenes, Macromol, 29, 6371-6376 (1996).
(Continued)

Primary Examiner — Caixia Lu
(74) Attorney, Agent, or Firm — Ballard Spahr LLP

(57) ABSTRACT

A catalyst in solid particulate form free from an external carrier material comprising
(I) a complex of formula (I)

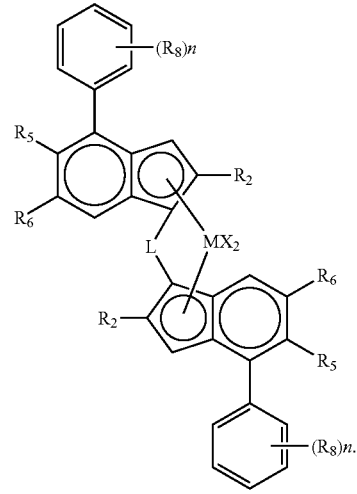

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;
each $R_2$ is independently hydrogen or a C1-C20 hydrocarbyl radical provided that at least one $R_2$ is not hydrogen;
each $R_5$ is independently hydrogen or a C1-20 hydrocarbyl group optionally containing one or more heteroatoms from groups 14-16;
each $R_6$ is independently hydrogen or a C1-20 hydrocarbyl group optionally containing one or more heteroatoms from groups 14-16;
each n is independently 1, 2 or 3; and
each $R_8$ is a C1-20 hydrocarbyl group;
and (ii) a cocatalyst comprising a compound of a group 13 metal, e.g. Al or boron.

10 Claims, No Drawings

(52) U.S. Cl.
CPC .......... *C08F 4/65927* (2013.01); *C08F 10/06* (2013.01); *C07C 2531/18* (2013.01); *C08F 4/65912* (2013.01)

(56) References Cited

U.S. PATENT DOCUMENTS

| | | | |
|---|---|---|---|
| 9,469,699 | B2 | 10/2016 | Resconi et al. |
| 2003/0149199 | A1 | 8/2003 | Schottek et al. |
| 2004/0260107 | A1 | 12/2004 | Oberhoff et al. |
| 2005/0239979 | A1 | 10/2005 | Schottek et al. |
| 2007/0135596 | A1 | 6/2007 | Voskoboynikov et al. |

FOREIGN PATENT DOCUMENTS

| | | | |
|---|---|---|---|
| EP | 1070729 | A2 | 1/2001 |
| EP | 1270614 | A2 | 1/2003 |
| EP | 1448578 | A1 | 8/2004 |
| EP | 1636245 | A1 | 3/2006 |
| EP | 1692144 | A2 | 8/2006 |
| EP | 2340649 | A1 | 7/2011 |
| EP | 2532687 | A2 | 12/2012 |
| EP | 2535372 | A1 | 12/2012 |
| WO | WO-01/48034 | | 7/2001 |
| WO | WO-02/02575 | | 1/2002 |
| WO | WO-02/02576 | | 1/2002 |
| WO | WO/02-02576 | A1 | 1/2002 |
| WO | WO-03/045551 | | 6/2003 |
| WO | WO-03/051934 | A2 | 6/2003 |
| WO | WO-2004/106351 | A1 | 12/2004 |
| WO | WO-2005/023889 | A1 | 3/2005 |
| WO | WO-2005/105863 | A2 | 11/2005 |
| WO | WO-2007/107448 | A1 | 9/2007 |
| WO | WO-2007/116034 | A1 | 10/2007 |
| WO | WO-2007/135596 | A1 | 11/2007 |
| WO | WO-2009/054831 | A1 | 4/2009 |
| WO | WO-2009/054832 | A1 | 4/2009 |
| WO | WO-2009/054833 | A2 | 4/2009 |
| WO | WO-2011/076433 | A2 | 6/2011 |
| WO | WO-2011/076617 | A1 | 6/2011 |
| WO | WO-2014/096164 | A1 | 6/2014 |
| WO | WO-2014/096166 | A1 | 6/2014 |
| WO | WO-2014/096171 | A1 | 6/2014 |
| WO | WO-2014/096282 | A1 | 6/2014 |

OTHER PUBLICATIONS

Elder et al., Synthesis and Performance of *ansa*-Metallocene Catalysts with substituted Heterocyclic and Indenyl Ligands, Kinetics and Catalysis, vol. 47, No. 2, 2006, 192-197.
Ewen, J. et al., Chiral *Ansa* Metallocenes with Cp Ring-Fused to Thiophenes and Pyrroles: Syntheses, Crystal Structures, and Isotactic Polypropylene Catalysts, J. Am. Chem. Soc. 2001, 123, 4763-4773.
Ewen, J. et al., Evaluation of the dimethylsiyl-bis(2-methyl-4-phenyl-1-indenyl) ligand with group 4 triad metals in propene polymerizations with methylaluminoxane, Macromol. Rapid Commun. 19, 71-73 (1998).
Izmer, V. et al., Palladium-Catalyzed Pathways to Aryl-Substituted Indenes: Efficient Synthesis of Ligands and the Respective *ansa*-Zirconocenes,Organometallics 2006, vol. 25, No. 5, pp. 1217-1229.
Nifant'ev, Ilya E. et al., 5-Methoxy-Substituted Zirconium Bisindenyl *ansa*-Complexes: Synthesis, Structure, and Catalytic Activity in the Polymerization and Copolymerization of Alkenes, Organometallics, vol. 31, No. 14, 4962-4970 (Jul. 23, 2012).
Nifant'ev, Ilya E. et al., Asymmetric *ansa*-Zirconocenes Containing a 2-Methyl-4-aryltetrahydroindacene Fragment: Synthesis, Structure, and Catalytic Activity in Propylene Polymerization and Copolymerization, Organometallics 2011, 30, 5744-5752.
Spaleck, W. et al., New Bridged zirconocenes for olefin polymerization: Binuclear and hybrid structures, Journal of Molecular Catalysis A: Chemical 128, 279-287 (1998).
Spaleck, W. et al., The Influence of Aromatic Substituents on the Polymerization Behavior of the Bridged Zirconocene Catalysts, Organometallics 1994, vol. 13, No. 3, 954-963.
International Search Report and Written Opinion mailed May 30, 2014 by the International Searching Authority for International Application No. PCT/EP2013/077344, which was published as WO 2014/096171 on Jun. 26, 2014 (Inventor—Castro et al.; Applicant—Borealis AG; (13 pages).
International Search Report and Written Opinion mailed May 27, 2014 by the International Searching Authority for International Application No. PCT/EP2013/077339, which was published as WO 2014/096166 on Jun. 26, 2014 (Inventor—Resconi et al.; Applicant—Borealis AG; (13 pages).
International Search Report and Written Opinion mailed May 30, 2014 by the International Searching Authority for International Application No. PCT/EP2013/077335, which was published as WO 2014/096164 on Jun. 26, 2014 (Inventor—Resconi, et al.; Applicant—Borealis AG; (15 pages).
International Search Report and Written Opinion mailed Mar. 3, 2014 by the International Searching Authority for International Application No. PCT/EP2013/077531, which was published as WO 2014/096282 on Jun. 26, 2014 (Inventor—Resconi, et al.; Applicant—Borealis AG; (10 pages).
U.S. Appl. No. 14/654,405, filed Jun. 19, 2015, Resconi, L. et al.
U.S. Appl. No. 14/654,409, filed Jun. 19, 2015, Resconi, L. et al.
U.S. Appl. No. 14/654,413, filed Jun. 19, 2015, Resconi, L. et al.
Notice of Allowance issued on Jun. 8, 2016 for U.S. Appl. No. 14/654,409, filed Jun. 19, 2015 (Applicant—Borealis AG // Inventor—Resconi, et al.) (5 pages).
Notice of Allowance issued by the USPTO on Nov. 2, 2016 for U.S. Appl. No. 14/654,405, filed on Jun. 19, 2015 and published a U.S. 2015/0344596 on Dec. 3, 2015 (Applicant—Borealis AG // Inventor—Resconi, et al) (9 pages).

CATALYST

CROSS-REFERENCE TO RELATED APPLICATIONS

This application is a U.S. National Phase Application of International Application No. PCT/EP2013/077344, filed on Dec. 19, 2013, which claims priority to European Patent Application No. 12199251.5, filed Dec. 21, 2012, each of which are hereby incorporated by reference in their entirety.

FIELD OF INVENTION

This invention relates to new bisindenyl catalysts, in particular, solid particulate racemic symmetrical metallocene catalysts containing such bisindenyl ligands. The invention also relates to the use of such new bisindenyl metallocene catalysts for the production of polypropylene at excellent catalyst activities to give polypropylene with high molecular weight, and very high melting point even at industrially relevant polymerization temperatures.

BACKGROUND OF INVENTION

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns. The two most important physical properties of isotactic polypropylene (iPP) are its average molecular weight and its melting point (Tm), the latter being mostly determined by the degree of stereoregularity (isotacticity) of the polypropylene chains.

The Ziegler-Natta catalyst systems known in the literature can produce iPP with high molecular weights together with moderate to high isotacticities and melting temperatures (Tm). The Tm (measured by standard DSC methods) of non-nucleated iPPs are in the range of 160 to 165° C.

In the case of metallocenes, there are very few examples which can produce iPP having both very high molecular weights and high melting points. For example rac-Et(2,4,7-Me$_3$Ind)$_2$ZrCl$_2$ can produce isotactic polypropylene with a molecular weight of 1,900,000 g/mol and a melting point of 168° C.

In order to achieve such high values, a polymerization temperature of −30° C. is necessary. When the polymerization temperature is increased to 30° C., the melting point of the resulting polypropylene decreases to 158° C. A polymerization temperature of −30° C. is however, far too low for polypropylene manufacturing in commercial plants, which need to be operated above 60° C. When used at industrially useful polymerization temperatures, this same metallocene yields low molecular weight polypropylenes with relatively low melting point. For example at 70° C., rac-Et(2,4,7-Me$_3$Ind)$_2$ZrCl$_2$/MAO yields a polypropylene of molecular weight of only 30,600 with a melting point of only 145° C.

In U.S. Pat. No. 7,405,261, rac-Et[2,7-Me$_2$-4-(4-tBuPh)Ind]$_2$ZrCl$_2$ is reported to produce iPP with a melting point of 156° C., by polymerizing liquid propylene at 65° C.

WO2009/054831 describes zirconocenes with a 2-methyl-4,7-aryl substitution pattern, such as rac-Me$_2$Si[2-Me-4,7-(4-tBuPh)$_2$Ind]$_2$ZrCl$_2$. The melting points of the homopolymers are still quite low, being in all cases below 150° C. despite the relatively low polymerization temperature of 65° C.

WO02/02576 describes conventionally supported metallocenes such as rac-Me$_2$Si[2-Me-4-(3,5-tBu$_2$Ph)Ind]$_2$ZrCl$_2$. These metallocene catalysts, activated with MAO or a borate, on a silica support, at a polymerisation temperature of 60 or 70° C., give iPP with Tm between 156 and 159° C.

The metallocene rac-9-silafluorenyl-9,9-[2-Me-4-(3,5-tBu$_2$Ph)Ind]$_2$ZrCl$_2$ also gives high melting point iPP and are described in WO02/02575.

In general however, metallocene catalysts, when used under industrially relevant polymerization conditions, produce iPP having melting points which are lower than the melting points of Ziegler Natta iPP, and even the best metallocene catalysts produce iPP with melting points of less than 160° C. In addition, few metallocene catalysts can produce iPP having both high melting point and high molecular weight at polymerisation temperatures above 60° C.

In order to overcome this inherent limitation of metallocene catalysts, and in order to produce polypropylenes having both high melting points and high molecular weights, we have developed a new family of catalysts comprising substituted bis-indenyl complexes.

Whilst the bisindenyl complexes of this invention are known, we employ these complexes in solid particulate yet unsupported form to make a new family of catalysts with interesting properties. These metallocenes have been found to produce isotactic polypropylenes with surprisingly high melting points and very high molecular weights.

The catalysts of the invention comprise a bridged bisindenyl metallocene complex with a substituted aryl group at the 4-position of an indenyl ligand and at least one non hydrogen substituent at the 2-position of the ring. The seven position is unsubstituted. Such complexes are known in the art in WO02/02576. However, the metallocene catalysts of WO02/025676, activated with MAO or a borate, are carried on a silica support. At polymerisation temperatures of 60 or 70° C. they give iPP with Tm between 156 and 159° C. but at very poor catalyst activity.

The present inventors sought a new catalyst system capable of producing, inter alia, isotactic polypropylene with high melting points, high isotacticity and high molecular weights without compromising catalyst activity at commercially relevant temperatures.

SUMMARY OF INVENTION

Thus, viewed from one aspect the invention provides a catalyst in solid particulate form free from an external carrier material comprising (i) a complex of formula (I)

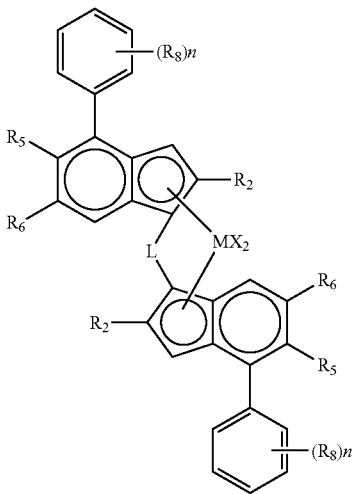

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;

each $R_2$ is independently hydrogen or a C1-C20 hydrocarbyl radical provided that at least one $R_2$ is not hydrogen;

each $R_5$ is independently hydrogen or a C1-20 hydrocarbyl group optionally containing one or more heteroatoms from groups 14-16;

each $R_6$ is independently hydrogen or a C1-20 hydrocarbyl group optionally containing one or more heteroatoms from groups 14-16;

each n is independently 1, 2 or 3;
each $R_8$ is a C1-20 hydrocarbyl group.
and (ii) a cocatalyst comprising a compound of a group 13 metal, e.g. Al or boron.

Ideally, the catalyst is obtainable by a process in which
(a) a liquid/liquid emulsion system is formed, said liquid/liquid emulsion system comprising a solution of the catalyst components (i) and (ii) dispersed in a solvent so as to form dispersed droplets; and
(b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;

forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined.

Viewed from another aspect the invention provides a process for the polymerisation of at least one olefin, in particular propylene, comprising polymerising said at least one olefin with a catalyst as hereinbefore described.

Viewed from another aspect the invention provides a process for producing an isotactic polypropylene with a melting point of at least 155° C. and at a catalyst activity of at least 10.0 kg/g(cat)/h comprising polymerising propylene in the presence of the catalyst as hereinbefore defined.

DEFINITIONS

Throughout the description the following definitions are employed.

By free from an external carrier is meant that the catalyst does not contain an external support, such as an inorganic support, for example, silica or alumina, or an organic polymeric support material, onto which catalyst components are loaded.

The term $C_{1-20}$ hydrocarbyl group includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

The term halo includes fluoro, chloro, bromo and iodo groups, especially chloro groups, when relating to the complex definition.

The term heterocyclic group means a preferably monocyclic non aromatic ring structure comprising at least one heteroatom, e.g. piperidinyl or piperazinyl.

The term heteroaryl means a preferably monocyclic aromatic ring structure comprising at least one heteroatom. Preferred heteroaryl groups have 1 to 4 heteroatoms selected from O, S and N. Preferred heteroaryl groups include furanyl, thiophenyl, oxazole, thiazole, isothiazole, isooxazole, triazole and pyridyl.

Any group including "one or more heteroatoms belonging to groups 14-16" preferably means O, S or N. N groups may present as —NH— or —NW— where R" is C1-10 alkyl. There may, for example, be 1 to 4 heteroatoms. That heteroatom might be at the end or in the middle of the group in question, e.g. forming O—Me.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced (kg)/g catalyst/h. Catalyst metal activity is defined here to be the amount of polymer produced (kg)/g Metal/h. The term productivity is also sometimes used to indicate the catalyst activity although herein it designates the amount of polymer produced per unit weight of catalyst.

DETAILED DESCRIPTION OF INVENTION

The catalysts of the invention comprise a complex of formula (I)

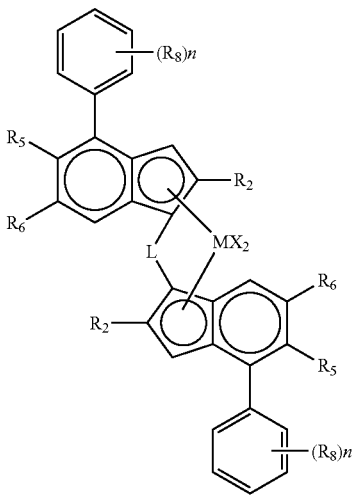

wherein

M is zirconium or hafnium;

each X is a sigma ligand;

L is a divalent bridge selected from —R'$_2$C—, —R'$_2$C—CR'$_2$—, —R'$_2$Si—, —R'$_2$Si—SiR'$_2$— and —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;

each R$_2$ is independently hydrogen or a C1-C20 hydrocarbyl radical provided that at least one R$_2$ is not hydrogen;

each R$_5$ is independently hydrogen or a C1-20 hydrocarbyl group optionally containing one or more heteroatoms from groups 14-16;

each R$_6$ is independently hydrogen or a C1-20 hydrocarbyl group optionally containing one or more heteroatoms from groups 14-16;

each n is independently 1, 2 or 3;

each R$_8$ is a C1-20 hydrocarbyl group.

The catalyst of the invention is not in supported form but is in solid particulate form. The term solid implies that the catalyst is solid at room temperature. The term particulate implies that the catalyst is a free flowing powder like material.

The two multicyclic ligands making up the complexes of the invention are preferably identical and hence the complexes of the invention may be symmetrical. The complexes of the invention are preferably in their racemic form. It is a feature of the invention, that the process described in detail below for the formation of the complexes of the invention gives rise to complexes predominantly in their rac form.

There is low or very low meso form of the complexes formed, e.g. less than 20 wt % thereof.

M is preferably Zr.

Each X, which may be the same or different, is preferably a hydrogen atom, a halogen atom, a R, OR, OSO$_2$CF$_3$, OCOR, SR, NR$_2$ or PR$_2$ group wherein R is a linear or branched, cyclic or acyclic, C1-C20-alkyl, C2-C20 alkenyl, C2-C20 alkynyl, C6-C20-aryl, C7-C20-alkylaryl or C7-C20-arylalkyl radical; optionally containing heteroatoms belonging to groups 14-16. R is preferably a C$_{1-6}$ alkyl, phenyl or benzyl group.

Most preferably each X is independently a hydrogen atom, a halogen atom, C$_{1-6}$-alkoxy group or an R group, e.g. preferably a C$_{1-6}$-alkyl, phenyl or benzyl group. Most preferably X is chlorine or a methyl radical. Preferably both X groups are the same.

In any L group, it is preferred if all R' groups are the same. L is preferably a bridge comprising a heteroatom, such as silicon or, germanium, e.g. —SiR$^9$$_2$—, wherein each R$^9$ is independently C1-C20-alkyl, C5-10 cycloalkyl, C6-C20-aryl or tri(C1-C20-alkyl)silyl-residue, such as trimethylsilyl. More preferably R$^9$ is C$_{1-6}$-alkyl, especially methyl. It is preferred if all R$^9$ groups are the same. Most preferably, L is a dimethylsilyl or diethylsilyl bridge. It may also be an ethylene or methylene bridge.

R$_2$ is preferably a C1-10 hydrocarbyl group such as C1-6-hydrocarbyl group. More preferably it is a linear or branched C1-20 alkyl group. More preferably it is a linear or branched C1-6 alkyl group, especially linear C1-6 alkyl group such as methyl or ethyl. Ideally R$_2$ is methyl.

At least one R$_8$ group is present on the Ph rings. It is preferred if all R$_8$ groups are the same. It is preferred however, if 2 such groups are present, i.e. n is 2. In particular, those groups should be positioned at the 3 and 5 positions of the Ph ring bound to the indenyl ligand.

R$_8$ is preferably a C1-20 hydrocarbyl group, such as a C1-20 alkyl group or C6-10 aryl group. R$_8$ groups can be the same or different, preferably the same. More preferably, R$_8$ is a C2-10 alkyl group such as C3-8 alkyl group. Highly preferred groups are tert butyl groups. It is preferred if the group R$_8$ is bulky, i.e. is branched. Branching might be alpha or beta to the Ph ring. Branched C3-8 alkyl groups are also favoured therefore.

Each R$_5$ is preferably hydrogen or a C1-10 alkyl group, such as methyl. Ideally R$_5$ is hydrogen.

Each R$_6$ is preferably hydrogen or a C1-10 alkyl group, such as methyl. Ideally R$_6$ is hydrogen.

Preferred complexes of the invention are therefore of formula (II)

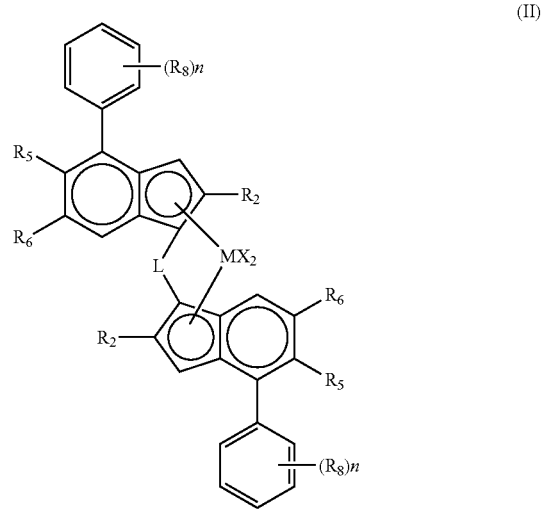

(II)

wherein

M is zirconium or hafnium;

each X is a sigma ligand, preferably each X is independently a hydrogen atom, a halogen atom, C$_{1-6}$-alkoxy group, C$_{1-6}$-alkyl, phenyl or benzyl group;

L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl; preferably dimethylsilyl, methylene or ethylene;

each R$_2$ is a C1-10 alkyl group;

each R$_5$ is hydrogen or a C1-10 alkyl group;

each $R_6$ is hydrogen or a C1-10 alkyl group;
n is 1 to 3, e.g. 2;
and each $R^8$ is a C1-20 hydrocarbyl group.

Still more preferred complexes of the invention are of formula (III):

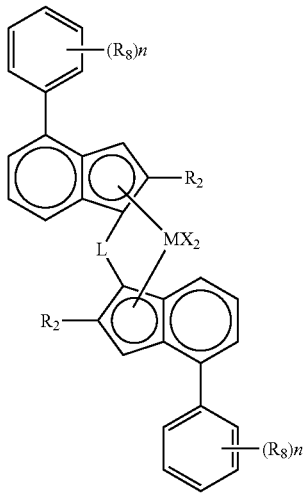

(III)

wherein
M is zirconium or hafnium;
each X is a sigma ligand, preferably each X is independently a hydrogen atom, a halogen atom, $C_{1-6}$-alkoxy group, $C_{1-6}$-alkyl, phenyl or benzyl group;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl; preferably dimethylsilyl;
$R_2$ is preferably a C1-10 alkyl group;
n is 1 to 3, e.g. 2;
and each $R^8$ is a C1-10 alkyl group or C6-10 aryl group.

Still more preferred complexes of the invention are of formula (IV)

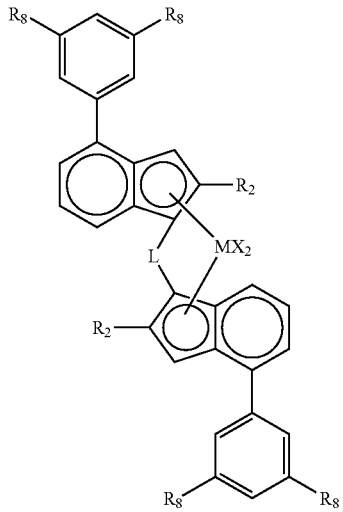

(IV)

wherein L, M and X are as hereinbefore defined (e.g. in formula (III));
$R_2$ is methyl; and
$R_8$ is C3-8 alkyl.

Highly preferred complexes of the invention are
rac-Me$_2$Si[2-Me-4(3,5-$^t$Bu$_2$Ph)-Ind]$_2$ZrCl$_2$.
rac-Me$_2$Si[2-Me-4(3,5-$^t$Bu$_2$Ph)-Ind]$_2$HfCl$_2$.

For the avoidance of doubt, any narrower definition of a substituent offered above can be combined with any other broad or narrowed definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the complexes and hence catalysts of the invention can be synthesised by any process and the skilled organic chemist would be able to devise various synthetic protocols for the manufacture of the necessary ligand materials. In particular WO02/02576 describes suitable synthetic protocols.

Ideally, the Ph group at the 4-position should carry at least two substituents, in particular substituents such as methyl, iso-propyl, neopentyl, tert-butyl or phenyl. Ideally, such bulky substituents are in the 3,5-positions of the 4-substituent. Ideally they are tert-butyl groups.

A conventional synthesis for ligands of formula (I) is given in WO02/02576. The key indene ligand precursor is shown in Scheme 1 below for the most preferred ligand uses herein:

Scheme 1: synthesis of 4-(3',5'-di-tertbutylphenyl)-2-methyl-indene

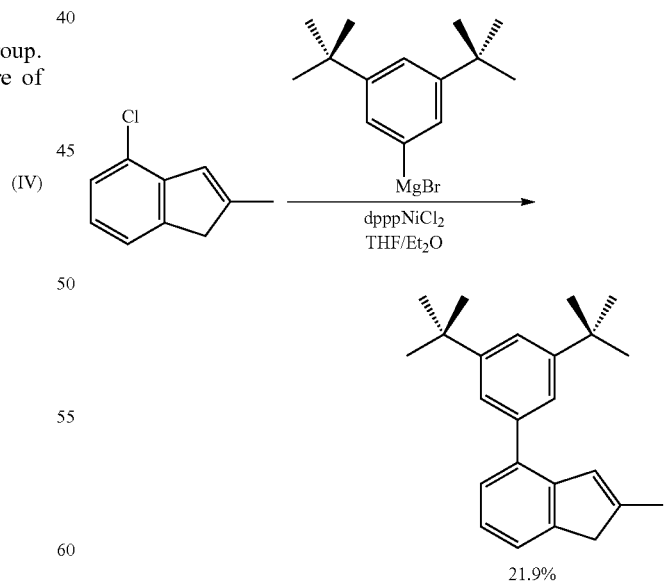

21.9%

The present inventors have devised a new procedure for the formation of this key intermediate which forms a further aspect of the invention.

The new procedure is shown in Scheme 2:

Scheme 2: synthesis of 7-(3′,5′-di-tertbutylphenyl)-2-methyl-indene

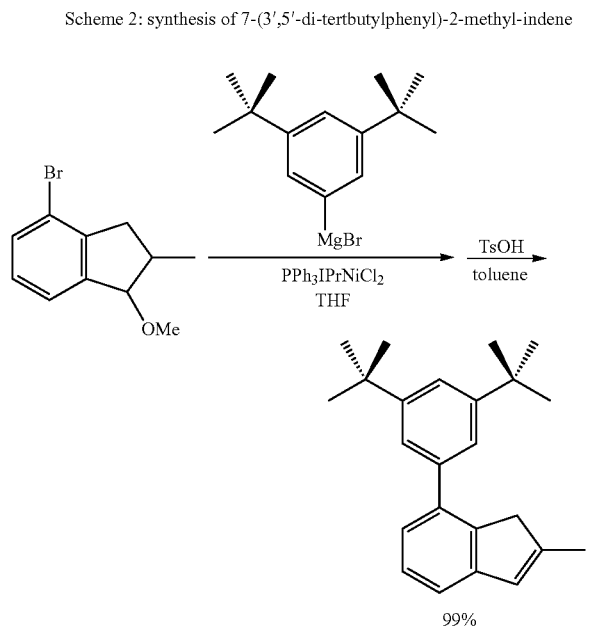

99%

The first step of this "one-pot" sequence is a Ni-catalyzed Kumada coupling, where the bromine atom in the indene 6-membered ring gets substituted with a di(tert-butyl)phenyl moiety). In order to obtain an indene i.e. formally eliminate MeOH and form a carbon-carbon double bond, an acid-catalyzed elimination using a dean-stark apparatus is used. TsOH can be used as an acid catalyst and toluene can be employed to remove water/methanol azeotropically This process seems to lead to a much higher yield of key intermediate.

Thus, viewed from another aspect the invention provides a process for the preparation of a compound of formula (V):

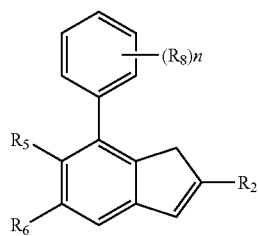

(V)

comprising at least the step of reacting a compound of formula (VI)

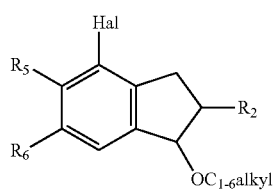

(VI)

with a compound (VII)

(VII)

wherein $R_2$, $R_5$, $R_6$, $R_8$ and n are as herein before defined, e.g. as in formulae (I) to (IV); and Hal is a halide, preferably Br;

in the presence of $PPh_3IPrNiCl_2$

In this reagent, IPr represents 1,3-bis(2,6-diisopropylphenyl)imidazolidin-2-ylidene. It is believed that other related imidazolidin-2-ylidene carbenes could also be used instead, e.g. those with groups other than 1,3-bis(2,6-diisopropylphenyl) such as 1,3-bis(2,4,6-trimethylphenyl). It will be appreciated that the reaction can take place in a solvent such as THF.

Preferably, this process further comprises a step of contacting the reaction product of compounds (VI) and (VII) with an acid catalyst such as tosyl alcohol. Again, that reaction can take place in a solvent such as toluene.

The alkoxy group in formula (VI) is preferably MeO—. The halide is preferably Br.

It will be appreciated that the ligand formed in this process is preferably that required to form the catalysts of formula (II), (III) or (IV). In a most preferred embodiment the ligand is

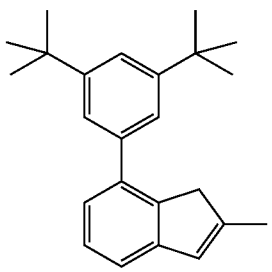 [SMILES: CC1=Cc2cccc(-c3cc(C(C)(C)C)cc(C(C)(C)C)c3)c2C1]

Cocatalyst

To form an active catalytic species it is normally necessary to employ a cocatalyst as is well known in the art. Cocatalysts comprising an organometallic compound of Group 13 metal, like organoaluminium compounds used to activate metallocene catalysts are suitable for use in this invention.

The olefin polymerisation catalyst system of the invention therefore comprises (i) a complex of the invention; and normally (ii) an aluminium alkyl compound (or other appropriate cocatalyst), or the reaction product thereof. Thus the cocatalyst is preferably an alumoxane, like MAO or an alumoxane other than MAO.

Alternatively, however, the catalysts of the invention may be used with other cocatalysts, e.g. boron compounds. It will be appreciated by the skilled man that where boron based cocatalysts are employed, it is normal to preactivate the complex by reaction thereof with an aluminium alkyl compound, such as TIBA. This procedure is well known and any suitable aluminium alkyl, e.g. $Al(C_{1-6}\text{-alkyl})_3$. can be used.

Boron based cocatalysts of interest include those of formula

wherein Y is the same or different and is a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for Y are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl. Preferred options are trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,5-dimethyl-phenyl)borane, tris(3,5-difluorophenyl)borane and/or tris(3,4,5-trifluorophenyl)borane.

Particular preference is given to tris(pentafluorophenyl) borane.

It is preferred however if borates are used, i.e. compounds containing a borate 3+ ion. Such ionic cocatalysts preferably contain a non-coordinating anion such as tetrakis(pentafluorophenyl)borate and tetraphenylborate. Suitable counterions are protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium.

Preferred ionic compounds which can be used according to the present invention include: triethylammoniumtetra(phenyl)borate, tributylammoniumtetra(phenyl)borate, trimethylammoniumtetra(tolyl)borate, tributylammoniumtetra(tolyl)borate, tributylammoniumtetra(pentafluorophenyeborate, tripropylammoniumtetra(dimethylphenyl)borate, tributylammoniumtetra(trifluoromethylphenyl)borate, tributylammoniumtetra(4-fluorophenyl)borate, N,N-dimethylcyclohexylammoniumtetrakis(pentafluorophenyl)borate, N,N-dimethylbenzylammoniumtetrakis(pentafluorophenyl)borate, N,N-dimethylaniliniumtetra(phenyl)borate, N,N-diethylaniliniumtetra(phenyl)borate, N,N-dimethylaniliniumtetrakis(pentafluorophenyl)borate, N,N-di(propyl)ammoniumtetrakis(pentafluorophenyl)borate, di(cyclohexyl)ammoniumtetrakist(pentafluorophenyl)borate, triphenylphosphoniumtetrakis(phenyl)borate, triethylphosphoniumtetrakis(phenyl)borate, diphenylphosphoniumtetrakis(phenyl)borate, tri(methylphenyl)phosphoniumtetrakis(phenyl)borate, tri(dimethylphenyl)phosphoniumtetrakis(phenyl)borate, triphenylcarbeniumtetrakis(pentafluorophenyl)borate, or ferroceniumtetrakis(pentafluorophenyl)borate. Preference is given to triphenylcarbeniumtetrakis(pentafluorophenyl)borate, N,N-dimethylcyclohexylammoniumtetrakis(pentafluorophenyl)borate or N5N-dimethylbenzylammoniumtetrakis(pentafluorophenyl)borate.

The use of $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4^{2-}$ is especially preferred.

Suitable amounts of borate cocatalyst will be well known to the skilled man.

The use of aluminoxanes, especially MAO, is highly preferred.

Suitable amounts of aluminoxane cocatalyst will be well known to the skilled man. Typically Al to M molar ratios are from 1:1 to 1000:1 mol/mol. Preferably when an aluminium alkyl is used as a coctalyst, the molar ratio of the aluminium in the activator to the transition metal in the complex is from 1 to 500 mol/mol, preferably from 10 to 400 mol/mol and in particular from 50 to 400 mol/mol.

Manufacture

The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst of the invention is in solid particulate form but unsupported, i.e. no external carrier is used. In order to provide the catalyst of the invention in solid form but without using an external carrier, it is preferred if a liquid liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape and particle size and without using any added external porous support material, such as an inorganic oxide, e.g. silica. Also desirable surface properties can be obtained.

By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e.g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e.g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr. 6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e.g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences are of e.g. 5 to 100° C., such as 10 to 100° C., or 20 to 90° C., such as 50 to 90° C.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i.e. an increase or a decrease in the temperature of an emulsion system, required for the desired solidification rate of the components cannot be limited to any specific range, but naturally depends on the emulsion system, i.a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e.g. as stated above, whereby said temperature change of the emulsion system is sufficient to cause the rapid solidification of the droplets. The receiving medium can be gaseous, e.g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e.g. perfluorinated hydrocarbon.

Alternatively, the temperature difference may be effected by gradual heating of the emulsion system, e.g. up to 10° C. per minute, preferably 0.5 to 6° C. per minute and more preferably in 1 to 5° C. per minute.

In case a melt of e.g. a hydrocarbon solvent is used for forming the dispersed phase, the solidification of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immiscibility can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e.g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e.g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e.g. by filtration and subsequent washing of the solids with a suitable solvent.

The droplet shape of the particles may be substantially maintained. The formed particles may have a mean size range of 1 to 500 µm, e.g. 5 to 500 µm, advantageously 5 to 200 µm or 10 to 150 µm. Even a mean size range of 5 to 60 µm is possible. The size may be chosen depending on the polymerisation the catalyst is used for. Advantageously, the mean particle size of the ready particulate catalysts of the invention are in the range of 2 to 150 µm, preferably 5 to 120 µm, more preferably 5 to 90 µm and especially in the range 10 to 70 µm. The particles are essentially spherical in shape, they have a low porosity and a low surface area.

The formation of solution can be effected at a temperature of 0-100° C., e.g. at 20-80° C. The dispersion step may be effected at −20° C.–100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The olefin polymerized using the catalyst of the invention is preferably propylene or a higher alpha-olefin or a mixture of ethylene and an α-olefin or a mixture of alpha olefins, for example $C_{2-20}$ olefins, e.g. ethylene, propylene, 1-butene, 1-hexene, 4-methyl-1-pentene, 1-octene etc. The olefins polymerized in the method of the invention may include any compound which includes unsaturated polymerizable groups. Thus, for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α, ω linear dienes such as 1,5-hexadiene, 1,6-heptadiene, 1,8-nonadiene, 1,9-decadiene, etc.

The catalysts of the present invention are particularly suited for use in the manufacture of polypropylene polymers, especially isotactic polypropylene.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours) The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

Generally the quantity of catalyst used will depend upon the nature of the catalyst, the reactor types and conditions and the properties desired for the polymer product. As is well known in the art hydrogen can be used for controlling the molecular weight of the polymer. It is particularly notable that the catalyst of the present invention performs exceptionally well over a wide range of hydrogen concentration used during the polymerisation process, which makes the catalyst beneficial to be used for productions of a wide range of polymers The catalysts are useful at higher hydrogen concentrations as well with lower hydrogen concentrations to get polymer with higher molecular weight. The activity of the catalysts of the invention is also very high and the polymer productivity levels are excellent.

It is a feature of the invention that the claimed catalysts enable the formation of polymers with remarkably high melting temperatures, Tm and with remarkably high molecular weight. These features can be achieved at commercially interesting polymerisation temperatures, e.g. 60° C. or more. It is a preferred feature of the invention that the catalysts of the invention are used to polymerise propylene at a temperature of at least 60° C., preferably at least 65° C., such as at least 70° C. It is also notable that catalysts of the present invention produce polymers with high melting temperatures, such as above 156° C. with clearly higher activity of the catalyst compared to catalysts of the prior art.

Catalyst activities may be of the order of 10.0 kg/g(cat)/h or more, such as 12 kg/g(cat)/h or more.

The catalysts of the invention enable the formation of high molecular weight polypropylene which also possess high isotacticity. Isotacticity is measured by 13C NMR or also by DSC. Thus, in the case of polypropylene homopolymers, isotacticity can be higher than 99.2% mm when measured by 13C NMR. When measured by standard DSC, the high isotacticity of the polypropylene homopolymers means a melting point (Tm) higher than 150° C., preferably higher than 152° C., even more preferably higher than 155° C.

The molecular weight of the polypropylene can be at least 300,000, preferably at least 400,000, especially at least 500,000. However, the molecular weight of the formed polymer is dependent on the amount of hydrogen employed, as is well known in the art.

Polypropylenes made by the metallocene catalysts of the invention can be made with $MFR_2$ values in the whole range of interest, that is from very high (as high as 2000, for example 1000 or 500) to very low, that is fractional values (<1). Hydrogen can be used to manipulate MFR as is well known.

The polymers made by the catalysts of the invention are useful in all kinds of end articles such as pipes, films (cast, blown and BOPP films), fibers, moulded articles (e.g. injection moulded, blow moulded, rotomoulded articles), extrusion coatings and so on. Film applications, such as those requiring BOPP (bi-oriented polypropylene) film, especially for capacitors are favoured.

The invention will now be illustrated by reference to the following non-limiting Examples.

Measurement Methods:

ICP Analysis

The elemental analysis of a catalyst was performed by taking a solid sample of mass, M, cooling over dry ice. Samples were diluted up to a known volume, V, by dissolving in nitric acid (HNO3, 65%, 5% of V) and freshly deionised (DI) water (5% of V). The solution was then added to hydrofluoric acid (HF, 40%, 3% of V), diluted with DI water up to the final volume, V, and left to stabilise for two hours.

The analysis was run at room temperature using a Thermo Elemental iCAP 6300 Inductively Coupled Plasma—Optical Emmision Spectrometer (ICP-OES) which was calibrated using a blank (a solution of 5% HNO3, 3% HF in DI water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of Hf and Zr in solutions of 5% HNO3, 3% HF in DI water.

Immediately before analysis the calibration is 'resloped' using the blank and 100 ppm Al, 50 ppm Hf, Zr standard, a quality control sample (20 ppm Al, 5 ppm Hf, Zr in a solution of 5% HNO3, 3% HF in DI water) is run to confirm the reslope. The QC sample is also run after every 5th sample and at the end of a scheduled analysis set.

The content of hafnium was monitored using the 282.022 nm and 339.980 nm lines and the content for zirconium using 339.198 nm line. The content of aluminium was monitored via the 167.079 nm line, when Al concentration in ICP sample was between 0-10 ppm (calibrated only to 100 ppm) and via the 396.152 nm line for Al concentrations above 10 ppm.

The reported values are an average of three successive aliquots taken from the same sample and are related back to the original catalyst by inputting the original mass of sample and the dilution volume into the software.

DSC Analysis

Melting temperature $T_m$ and crystallization temperature $T_c$ were measured on approx. 5 mg samples with a Mettler-Toledo 822e differential scanning calorimeter (DSC), according to ISO11357-3 in a heat/cool/heat cycle with a scan rate of 10° C./min in the temperature range of +23 to +225° C. under a nitrogen flow rate of 50 ml $min^{-1}$. Melting and crystallization temperatures were taken as the endotherm and exotherm peaks, respectively in the second heating and in the cooling step. Calibration of the instrument was performed with $H_2O$, Lead, Tin, Indium, according to ISO 11357-1.

Melt Flow Rate

The melt flow rate (MFR) is determined according to ISO 1133 and is indicated in g/10 min. The MFR is an indication of the flowability, and hence the processability, of the molten polymer. The higher the melt flow rate, the lower the viscosity of the polymer. The MFR is determined at 230° C. and may be determined at different loadings such as 2.16 kg ($MFR_2$) or 21.6 kg ($MFR_{21}$).

GPC: Molecular weight averages, molecular weight distribution, and polydispersity index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1× G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 μL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Quantification of Polypropylene Homopolymer Microstructure by NMR Spectroscopy

Quantitative nuclear-magnetic resonance (NMR) spectroscopy was used to quantify the isotacticity and content of regio-defects of the polypropylene homopolymers. Quantitative $^{13}C\{^1H\}$ NMR spectra recorded in the solution-state using a Bruker Advance III 400 NMR spectrometer operating at 400.15 and 100.62 MHz for $^1H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,2-tetrachloroethane-$d_2$ (TCE-$d_2$). This setup was chosen primarily for the high resolution needed for tacticity distribution quantification (Busico, V., Cipullo, R., Prog. Polym. Sci. 26 (2001) 443; Busico, V.; Cipullo, R., Monaco, G., Vacatello, M., Segre, A. L., Macromolecules 30 (1997) 6251). Standard single-pulse excitation was employed utilising the NOE and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun 2007, 28, 11289). A total of 8192 (8 k) transients were acquired per spectra. Quantitative $^{13}C\{^1H\}$ NMR spectra were processed, integrated and relevant quantitative properties determined from the integrals using proprietary computer programs. All chemical shifts are internally referenced to the methyl signal of the isotactic pentad mmmm at 21.85 ppm.

The tacticity distribution was quantified through integration of the methyl region between 23.6 and 19.7 ppm correcting for any sites not related to the stereo sequences of interest (Busico, V., Cipullo, R., Prog. Polym. Sci. 26 (2001) 443; Busico, V., Cipullo, R., Monaco, G., Vacatello, M., Segre, A. L., Macromolecules 30 (1997) 6251). The pentad isotacticity was determined through direct integration of the methyl region and reported as either the mole fraction or percentage of isotactic pentad mmmm with respect to all steric pentads i.e. [mmmm]=mmmm/sum of all steric pentads. When appropriate integrals were corrected for the presence of sites not directly associated with steric pentads.

Characteristic signals corresponding to regio irregular propene insertion were observed (Resconi, L., Cavallo, L., Fait, A., Piemontesi, F., Chem. Rev. 2000, 100, 1253). The presence of secondary inserted propene in the form of 2,1 erythro regio defects was indicated by the presence of the two methyl signals at 17.7 and 17.2 ppm and confirmed by the presence of other characteristic signals. The amount of 2,1 erythro regio defects was quantified using the average integral (e) of the e6 and e8 sites observed at 17.7 and 17.2 ppm respectively, i.e. e=0.5*(e6+e8). Characteristic signals corresponding to other types of regio irregularity were not observed (Resconi, L., Cavallo, L., Fait, A., Piemontesi, F., Chem. Rev. 2000, 100, 1253). The amount of primary inserted propene (p) was quantified based on the integral of all signals in the methyl region (CH3) from 23.6 to 19.7 ppm paying attention to correct for other species included in the integral not related to primary insertion and for primary insertion signals excluded from this region such that p=CH3+2*e. The relative content of a specific type of regio defect was reported as the mole fraction or percentage of said regio defect with respect all observed forms of propene insertion i.e. sum of all primary (1,2), secondary (2,1) and tertiary (3,1) inserted propene units, e.g. [21e]=e/(p+e+t+i). The total amount of secondary inserted propene in the form of 2,1-erythro or 2,1-threo regio defects was quantified as sum of all said regio irregular units, i.e. [21]=[21e]+[21t].

Catalyst Activity

The catalyst activity (A Cat) was calculated on the basis of following formula:

$$\text{Catalyst Activity } (kg)/(g(cat)*h)) = \frac{\text{amount of polymer produced (kg)}}{\text{catalyst loading (g)} \times \text{polymerisation time (h)}}$$

Catalyst Metal Activity (A Mt) was calculated on the basis of following formula:

$$\text{Catalyst Metal Activity } (kg/(g(cat)*h)) = \frac{\text{amount of polymer produced (kg)}}{\text{catalyst metal loading (g)} \times \text{polymerisation time (h)}}$$

EXAMPLES

Chemicals

All the chemicals and chemical reactions were handled under an inert gas atmosphere using Schlenk and glovebox techniques, with oven-dried glassware, syringes, needles or cannulas.

MAO was purchased from Albermarle and used as a 30 wt-% solution in toluene.

The mixture of perfluoroalkylethyl acrylate esters (CAS 65605-70-1) used as the surfactant was purchased from the Cytonix corporation, dried over activated molecular sieves (2 times) and degassed by argon bubbling prior to use.

Perfluoro-1,3-dimethylcyclohexane (PFC, CAS 335-27-3) was dried over activated molecular sieves (2 times) and degassed by argon bubbling prior to use.

Triethylaluminum was purchased from Crompton and used in pure form. Hydrogen is provided by AGA and purified before use.

Propylene is provided by Borealis and adequately purified before use. 2 M HCl, 12 M HCl (Reachim, Russia), silica gel 60 (40-63 um, Merck), $K_2CO_3$ (Merck), $ZrCl_4(THF)_2$ magnesium turnings (Acros), TsOH (Aldrich), nBuLi (Chemetall), n-hexane (Merck), were used as received. Toluene (Merck), THF (Merck), dichloromethane (Merck), were kept and distilled over Na/K alloy. Dichlorodimethylsilane (Merck) was distilled before use. $CDCl_3$, $DMSO-d_6$ and $CD_2Cl_2$ (Deutero GmbH) for NMR experiments were dried and kept over $CaH_2$. methyl iodide (Acros) 1-bromo-3,5-di-tert-butylbenzene (Aldrich) has been used as received. Bis (2,6-diisopropylphenyl)imidazolium chloride, i.e. IPr(HCl), and $(IPr)NiCl_2(PPh_3)$ were synthesized as described in [Hintermann, L. Beilstein J. Org. Chem. 2007, 3, 1.] and [Matsubara, K.; Ueno, K.; Shibata, Y. Organometallics 2006, 25, 3422.], respectively. 4-Bromo-1-methoxy-2-methylindane was obtained as described in [Izmer, V. V.; Lebedev, A. Y.; Nikulin, M. V.; Ryabov, A. N.; Asachenko, A. F.; Lygin, A. V.; Sorokin, D. A.; Voskoboynikov, A. Z. Organometallics 2006, 25, 1217.].

rac-dimethylsilanediylbis(2-methyl-4-phenylindenyl) zirconium dichloride, is described e.g. in EP-A-0576970, has CAS no 153882-67-8 and provided by Norquaytech.

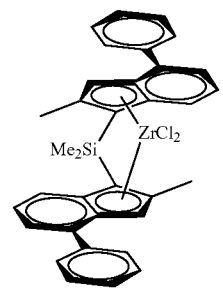

rac-dimethylsilanediylbis(2-methyl-4-(3,5-di-tert-butylphenyl)-7-methoxyindenyl) zirconium dichloride, has been synthesized as described by Schöbel, Rieger et al. in Chemistry-A European Journal, vol. 18, pages 4174-4178 (2012).

Catalyst Preparation 1

Catalyst complex synthesis of rac-Me$_2$Si[2-Me-4-(3,5-$^t$Bu$_2$Ph)Ind]$_2$ZrCl$_2$—MC1

7-(3,5-di-tert-butylphenyl)-2-methyl-1H-indene

To a solution of 3,5-di-tert-butylphenylmagnesium bromide obtained from 29.6 g (0.110 mol) of 1-bromo-3,5-di-tert-butylbenzene and 3.80 g (0.156 mol) of magnesium turnings in 200 ml of THF, 0.40 g (0.512 mmol, 0.5 mol.%) of NiCl$_2$(PPh$_3$)(IPr) and 24.1 g (0.10 mol) of 4-bromo-1-methoxy-2-methylindane were added. A vigorous reflux occurred approximately after 30 sec which ceased after the following 30 sec. This mixture was stirred at room temperature for 30 min. Finally, 1000 ml of water and then 50 ml of 12 M HCl were added. The product was extracted with 500 ml of dichloromethane, organic layer was separated, the aqueous layer was additionally extracted with 2×150 ml of dichloromethane. The combined organic extract was dried over K$_2$CO$_3$ and evaporated to dryness. To the residue dissolved in 300 ml of toluene 0.4 g of TsOH was added. The resulting solution was refluxed using Dean-Stark head for 15 min, then another 0.5 g of TsOH was added, and the obtained mixture was refluxed for 0.5 h. The reaction mixture was cooled to room temperature and then washed by 200 ml of 10% aqueous K$_2$CO$_3$.

The organic layer was separated, the aqueous layer was additionally extracted with 2×100 ml of dichloromethane. The combined organic extract was evaporated to dryness. The product was isolated by flash chromatography on silica gel 60 (40-63 µm; eluent: hexane, then hexane/dichloromethane=10:1, vol.). This procedure gave 31.9 g (99%) of 7-(3,5-di-tert-butylphenyl)-2-methyl-1H-indene as a white crystalline powder. The latter was recrystallized from n-hexane with almost no loss in mass.

Anal. calc. for C$_{24}$H$_{30}$: C, 90.51; H, 9.49. Found: C, 90.48; H, 9.44.

$^1$H NMR (CDCl$_3$): δ 7.41 (t, J=1.8 Hz, 1H, 4-H in 3,5-tBu$_2$C$_6$H$_3$), 7.37 (d, J=1.8 Hz, 2H, 2,6-H in 3,5-tBu$_2$C$_6$H$_3$), 7.31 (t, J=7.5 Hz, 1H, 5-H in indene), 7.24 (dd, J=7.5 Hz, J=1.0 Hz, 1H, 6-H in indene), 7.15 (dd, J=7.5 Hz, J=1.1 Hz, 1H, 4-H in indene), 6.54 (m, 1H, 3-H in indene), 3.38 (m, 2H, 1,1'-H in indene), 2.14 (m, 3H, 2-Me in indene), 1.38 (s, 18H, tBu).

Bis[4-(3,5-di-tert-butylphenyl)-2-methyl-1H-inden-1-yl]dimethylsilane 15.0 ml (37.5 mmol) of 2.5 M nBuLi in hexanes was added in one portion at room temperature to a solution of 11.9 g (37.5 mmol) of 7-(3,5-di-tert-butylphenyl)-2-methyl-1H-indene in 200 ml of toluene. This mixture was stirred overnight at room temperature, then 10 ml of THF was added, and the resulting mixture was refluxed for 2 h. The resulting mixture was cooled to room temperature, and 2.42 g (18.8 mmol) of dichlorodimethylsilane was added in one portion. Further on, this mixture was refluxed for 1 h, then 0.5 ml of water was added, and the formed solution was filtered through a pad of silica gel 60 (40-63 µm) which was additionally washed by dichloromethane. The combined organic elute was evaporated to dryness and dried in vacuum. This procedure gave 13.0 g (100% of ca. 90% purity) of bis[4-(3,5-di-tert-butylphenyl)-2-methyl-1H-inden-1-yl]dimethylsilane as a yellowish glass. This product was further used without an additional purification.

Anal. calc. for C$_{50}$H$_{64}$Si: C, 86.64; H, 9.31. Found: C, 87.05; H, 9.55.

$^1$H NMR (CDCl3): δ 7.21-7.57 (m), 6.89 (m), 6.88 (m), 3.91 (s), 3.87 (s), 2.31 (s), 2.29 (s), 1.45 (s), 1.44 (s), −0.13 (s), −0.15 (s), −0.19 (s).

Rac-dimethylsilanediylbis[4-(3,5-di-tert-butylphenyl)-2-methyl-1H-inden-1-yl]zirconium dichloride (Complex MC1)

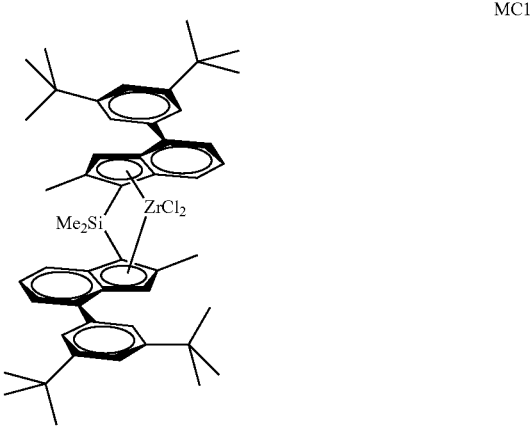

MC1

To a solution of 10.7 g (15.4 mmol) of bis[4-(3,5-di-tert-butylphenyl)-2-methyl-1H-inden-1-yl]dimethylsilane in 150 ml of toluene, 12.3 ml (30.8 mmol) of 2.5 M nBuLi in hexanes was added in one portion at room temperature. This mixture was stirred overnight at room temperature, the resulting light orange solution was then cooled to −25° C., and 5.81 g (15.4 mmol) of ZrCl$_4$(THF)$_2$ was added. The resulting dark red mixture was stirred for 24 h, then 10 ml of THF was added. The obtained mixture was stirred for 2 h at 60° C. After evaporation of ca. 50 ml of the solvents, the resulting solution warmed to 80° C. was filtered through glass frit (G4). The filtrate was evaporated to dryness, and then 250 ml of n-hexane was added to the residue. The obtained suspension was stirred overnight at room temperature and then filtered through a glass frit (G3). The filtrate was evaporated to dryness, and 25 ml of n-hexane was added to the residue. The formed yellow precipitate was filtered off, washed with 5×15 ml of n-hexane, and dried in vacuum. This procedure gave rac-zirconocene contaminated with ca. 4% of meso-form. To purify it, this product was dissolved in 20 ml of hot toluene, and to the obtained solution 100 ml of n-hexane was added. The formed precipitate was filtered off and then dried in vacuum. This procedure gave 2.29 g (17%) of pure rac-complex.

Anal. calc. for C$_{50}$H$_{62}$Cl$_2$SiZr: C, 70.38; H, 7.32. Found: C, 70.29; H, 7.38.

$^1$H NMR (CDCl$_3$): δ 7.66 (d, J=8.4 Hz, 2H, 5-H in indenyl), 7.54 (m, 4H, 2,6-H in 3,5-tBu$_2$C$_6$H$_3$), 7.40-7.43 (m, 4H, 7-H in indenyl and 4-H in 3,5-tBu$_2$C$_6$H$_3$), 7.12 (dd, J=8.4 Hz, J=6.9 Hz, 2H, 6-H in indenyl), 6.97 (s, 2H, 3-H in indenyl), 2.26 (s, 6H, 2-Me in indenyl), 1.34 (s, 6H, SiMe$_2$), 1.32 (s, 36H, tBu).

Catalyst Example E1—rac-Me$_2$Si[2-Me-4-(3,5-$^t$Bu$_2$Ph)Ind]$_2$ZrCl$_2$ (MC1)

Inside the glovebox, 80 µL, of dry and degassed surfactant solution were mixed with 2 mL of MAO in a septum bottle and left to react overnight. The following day, 64.9 mg of the metallocene rac-Me$_2$Si[2-Me-4-(3,5-$^t$Bu$_2$Ph)Ind]$_2$ZrCl$_2$/MAO (0.076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately (measured emulsion stability=17 seconds) and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.45 g of a red free flowing powder was obtained.

Comparative Example CE1—As Metallocene Is Used rac-dimethylsilanediylbis(2-methyl-4-phenyl-indenyl) zirconium dichloride Inside the glovebox, 80 µL, of dry and degassed surfactant solution were mixed with 2 mL of MAO in a septum bottle and left to react overnight. The following day, 47.8 mg of the metallocene. rac-dimethylsilanediylbis(2-methyl-4-phenyl-indenyl) zirconium dichloride, (0.076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately (measured emulsion stability=20 seconds) and stirred during 15 minutes at 0° C./600 rpm.

Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.51 g of a red free flowing powder was obtained.

Comparative Example CE2—As Metallocene Is Used rac-Me$_2$Si[2-Me-4-(3,5-$^t$Bu$_2$Ph)-7-OMe-Ind]$_2$ ZrCl$_2$ Inside the glovebox, 80 µL of dry and degassed surfactant solution were mixed with 2 mL of MAO in a septum bottle and left to react overnight. The following day, 69.4 mg of the metallocene, rac-Me$_2$Si[2-Me-4-(3,5-$^t$Bu$_2$Ph)-7-OMe-Ind]$_2$ ZrCl$_2$/MAO, (0,076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately (measured emulsion stability=16 seconds) and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.74 g of a red free flowing powder was obtained.

Catalyst properties are described in Table 1

TABLE 1

| Catalyst name | Zr (%) | Al (%) | Al/Zr (molar) |
|---|---|---|---|
| E1 | 0.29 | 24.0 | 280 |
| CE1 | 0.25 | 18.6 | 251 |
| CE2 | 0.29 | 23.70 | 276 |

Polymerisations

The polymerisations were performed in a 5 L reactor. 200 µl of triethylaluminum was fed as a scavenger in 5 mL of dry and degassed pentane. The desired amount of hydrogen was then loaded (measured in mmol) and 1100 g of liquid propylene was fed into the reactor.

Procedure A: The temperature was set to 30° C. The desired amount of catalyst (3 to 30 mg) in 5 mL of PFC is flushed into the reactor with a nitrogen overpressure. The temperature is then raised to 70° C. over a period of 15 minutes. The polymerisation is stopped after 30 minutes by venting the reactor and flushing with nitrogen before the polymer is collected.

Procedure B: The temperature was set to 20° C. The desired amount of catalyst (3 to 30 mg) in 5 mL of PFC is flushed into the reactor with a nitrogen overpressure. After 5 minutes of the temperature is raised to 70° C. over a period of 15 minutes. The polymerisation is stopped after 60 minutes by venting the reactor and flushing with nitrogen before the polymer is collected.

The catalyst activity (A Cat) was calculated on the basis of the 30 (or 60) minutes period according to the following formula:

$$\text{Catalyst Activity } (kg/(g(cat)*h)) = \frac{\text{amount of polymer produced (kg)}}{\text{catalyst loading (g)} \times \text{polymerisation time (h)}}$$

Catalyst Metal Activity (A Mt) was calculated on the basis of following formula:

$$\text{Catalyst Metal Activity } (kg/(g(cat)*h)) = \frac{\text{amount of polymer produced (kg)}}{\text{catalyst metal loading (g)} \times \text{polymerisation time (h)}}$$

Polymerisation results are disclosed in table 2

TABLE 2 polymerization results with catalyst CE1, CE2 and E1

| Catalyst Type | Cat. (mg) | Time min | $H_2$ mmol | Pol. Yield, g | A cat kg/g/h | A Mt kg/gMt/h | $MFR_2$ g/10$^6$ | $M_w$ kg/mol | $M_w/M_n$ | $T_m$ (° C.) | $T_c$ (° C.) |
|---|---|---|---|---|---|---|---|---|---|---|---|
| CE1 | 13.5 | 30 | 1 | 61 | 9.1 | 3639 | 3.6** | 676 | 2.4 | 149.3 | 110.5 |
|  | 12.3 | 30 | 6 | 80 | 13.1 | 5229 | 53.0** | 392 | 2.3 | 151.3 | 109.3 |
|  | 32.4 | 30 | 15 | 329 | 20.3 | 8116 | 4.5 | 240 | 2.4 | 150.0 | 109.7 |
| CE2 | 18.3 | 30 | 1 | 50 | 5.5 | 1888 | 1.9 | 347 | 2.0 | 159.4 | 113.5 |
|  | 16.1 | 30 | 6 | 120 | 15.0 | 5157 | 19.0 | 190 | 2.1 | 156.2 | 113.8 |
|  | 13.6 | 30 | 15 | 114 | 16.8 | 5781 | 120 | 106 | 2.2 | 156.6 | 116.5 |
| E1 | 11.1 | 60* | 1 | 99 | 9.0 | 3088 | 9.4** | 574 | 2.5 | 156.5 | 111.9 |
|  | 5.5 | 60* | 6 | 100 | 18.2 | 6270 | 1.9 | 302 | 2.4 | 158.9 | 112.2 |
|  | 10.7 | 60* | 15 | 218 | 20.4 | 7025 | 21.0 | 179 | 2.4 | 156.6 | 112.7 |

*procedure B,
**$MFR_{21}$ (g/10 min)

As can be seen higher Tm and at the same time higher activity are obtained by the catalyst of the invention. NMR results are disclosed in Table 3

| Catalyst | mmmm % | 2,1e % |
|---|---|---|
| E1 | 99.35 | 0.41 |
| CE1 | 99.14 | 0.98 |
| CE2 | 99.06 | 0.45 |

Comparative Example CE3 and CE4—Conventionally Silica Supported rac-Me$_2$Si[2-Me-4-(3,5-$^t$Bu$_2$Ph)Ind]$_2$ZrCl$_2$ Melting temperature and activity of the catalyst of the invention can be further compared to the catalyst of the same metallocene complex (MC-1), but supported on silica support. This supported catalyst has been disclosed in WO02/02576. Results are disclosed in Tables 6 and 8 of WO02/02576, and for comparison are used results of examples 32 and 42 of WO02/02576.

Catalyst Performance

As shown in Table 4 below, the catalyst of the invention shows significantly higher activity, at comparable MFR, than the comparison catalysts CE3, CE4 and CE2, while maintaining the high melting point.

TABLE 4

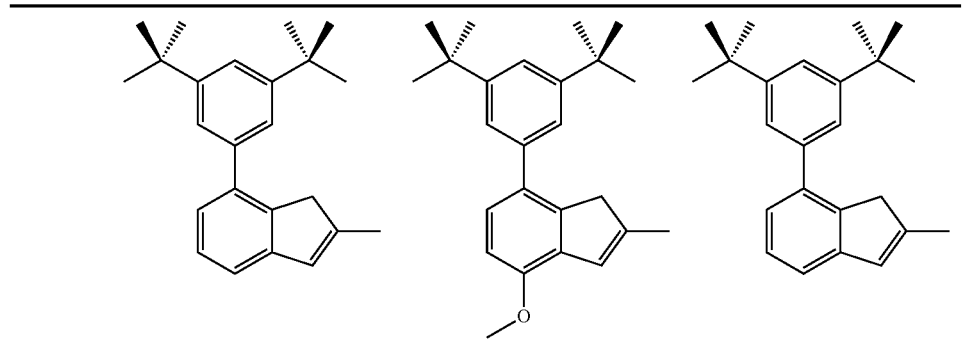

| Ligand | CE3 | CE4 | CE2 | E1-invention |
|---|---|---|---|---|
| cocatalyst | MAO | Borate | MAO | MAO |
| carrier | SiO$_2$ | SiO$_2$ | Solid no carrier | Solid no carrier |
| $T_p$* | 70 | 70 | 70 | 70 |
| MFR | 6.9 | 14.7 | 19 | 21 |
| $T_m$ | 157.4 | 159.1 | 156.2 | 156.6 |
| kg/g(cat)/h | 6.0 | 4.9 | 15.0 | 20.4 |
| kg/g(Zr)/h | 3300 |  | 5160 | 7025 |
| source | WO0202576 Tab 6, Ex 32 | WO0202576 Tab 8, ex 42 | CE2 | This invention |

$T_p$* = polymerisation temperature

The invention claimed is:

1. A catalyst in solid particulate form free from an external carrier material comprising
   (i) a complex of formula (I)

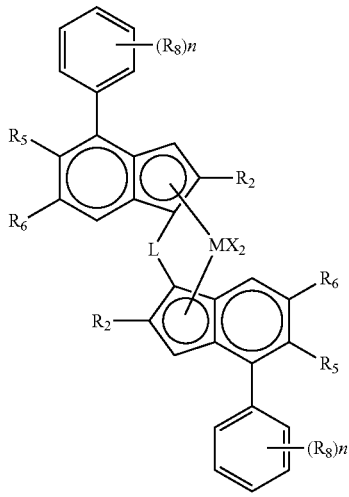

(I)

wherein
   M is zirconium or hafnium;
   each X is a sigma ligand;
   L is dimethylsilyl, diethylsilyl, ethylene or methylene;
   each $R_2$ is independently hydrogen or a C1-C20 hydrocarbyl radical provided that at least one $R_2$ is not hydrogen;
   each $R_5$ is independently hydrogen or a C1-20 hydrocarbyl group optionally containing one or more heteroatoms from groups 14-16;
   each $R_6$ is independently hydrogen or a C1-20 hydrocarbyl group optionally containing one or more heteroatoms from groups 14-16;
   each n is independently 1, 2 or 3; and
   each $R_8$ is a C1-20 hydrocarbyl group;
   and (ii) a cocatalyst comprising a compound of a group 13 metal.

2. The catalyst of claim 1 which is obtained by a process in which
   (a) a liquid/liquid emulsion system is formed, said liquid/liquid emulsion system comprising a solution of the catalyst components (i) and (ii) dispersed in a solvent so as to form dispersed droplets; and
   (b) solid particles are formed by solidifying said dispersed droplets.

3. A catalyst as claimed in claim 1 comprising a complex of formula

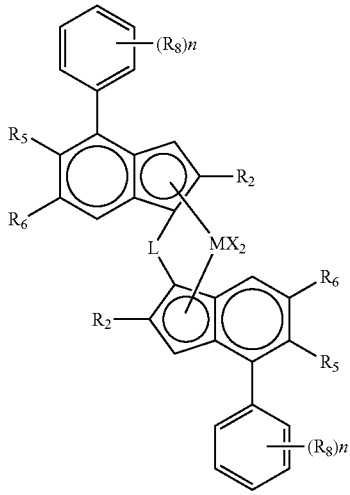

wherein
   M is zirconium or hafnium;
   each X is a sigma ligand;
   L is dimethylsilyl, diethylsilyl, ethylene or methylene;
   each $R_2$ is independently hydrogen or a C1-C20 hydrocarbyl radical provided that at least one $R_2$ is not hydrogen;
   each $R_5$ is independently hydrogen or an aliphatic C1-20 hydrocarbyl group;
   each $R_6$ is independently hydrogen or an aliphatic C1-20 hydrocarbyl group;
   n is 1, 2 or 3; and
   each $R_8$ is an aliphatic C1-20 hydrocarbyl group.

4. A catalyst as claimed in claim 1 comprising a complex of formula (II)

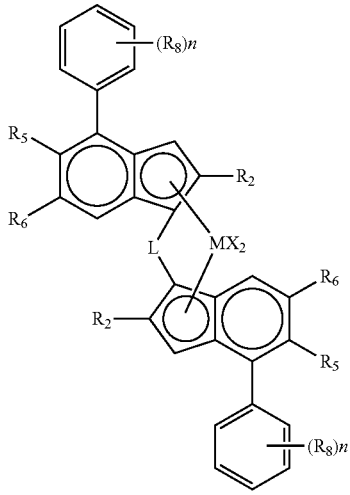

(II)

wherein
   M is zirconium or hafnium;
   each X is independently a hydrogen atom, a halogen atom, $C_{1-6}$-alkoxy group, $C_{1-6}$-alkyl, phenyl or benzyl group;
   L is dimethylsilyl, diethylsilyl, ethylene or methylene;
   each $R_2$ is a C1-10 alkyl group;
   each $R_5$ is hydrogen or a C1-10 alkyl group;

each $R_6$ is hydrogen or a C1-10 alkyl group;
n is 1 to 3;
and each $R^8$ is a C1-20 hydrocarbyl group.

5. A catalyst as claimed in claim 1 comprising a complex of formula (III):

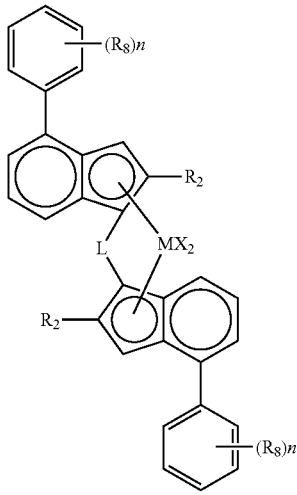

(III)

wherein
M is zirconium or hafnium;
each X is independently a hydrogen atom, a halogen atom, $C_{1-6}$-alkoxy group, $C_{1-6}$-alkyl, phenyl or benzyl group;
L is dimethylsilyl, diethylsilyl, ethylene or methylene;
$R_2$ is a C1-10 alkyl group;
n is 1 to 3;
and each $R^8$ is a C1-10 alkyl group or C6-10 aryl group.

6. A catalyst as claimed in claim 1 comprising a complex of formula (IV)

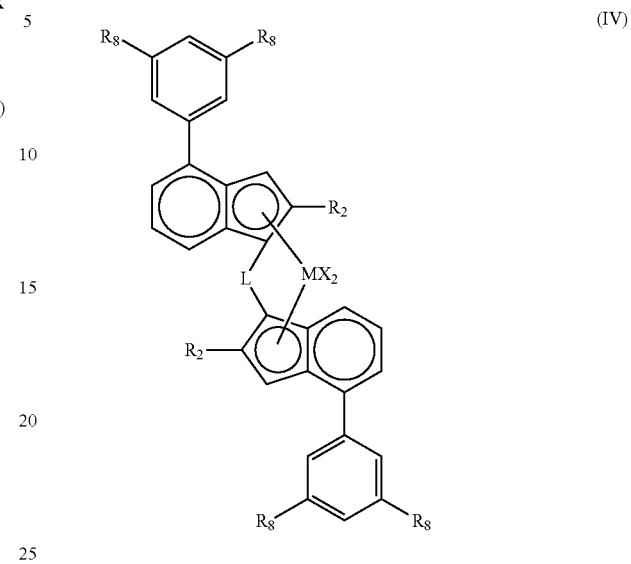

(IV)

wherein L, M and X are as hereinbefore defined;
$R_2$ is methyl; and
$R_8$ is C3-8 alkyl.

7. A catalyst as claimed in claim 1 wherein L is dimethylsilyl, ethylene or methylene.

8. A catalyst as claimed in claim 1 comprising the complex rac-Me$_2$Si[2-Me-4(3,5-$^t$Bu$_2$Ph)-Ind]$_2$ZrCl$_2$ or rac-Me$_2$Si[2-Me-4(3,5-$^t$Bu$_2$Ph)-Ind]$_2$HfCl$_2$.

9. A catalyst as claimed in claim 1 wherein said cocatalyst is aluminoxane.

10. A catalyst as claimed in claim 1 wherein the two ligands forming the complex are identical.

* * * * *